United States Patent [19]

Watanabe et al.

[11] 4,248,968

[45] Feb. 3, 1981

[54] PROCESS FOR PRODUCING ACRYLAMIDE OR METHACRYLAMIDE UTILIZING MICROORGANISMS

[75] Inventors: Ichiro Watanabe; Yoshiaki Satoh; Takayuki Takano, all of Yokohama, Japan

[73] Assignee: Nitto Chemical Industry Co., Ltd., Tokyo, Japan

[21] Appl. No.: 24,832

[22] Filed: Mar. 28, 1979

[30] Foreign Application Priority Data

Mar. 29, 1978 [JP] Japan .................................. 53-35318
Apr. 28, 1978 [JP] Japan .................................. 53-51236
Apr. 28, 1978 [JP] Japan .................................. 53-51237

[51] Int. Cl.³ .......................................... C12P 13/02
[52] U.S. Cl. ................................. 435/129; 435/227; 435/288; 435/813; 435/843; 435/822; 435/832; 435/840; 435/859; 435/872
[58] Field of Search ............... 435/129, 227, 288, 813

[56] References Cited

U.S. PATENT DOCUMENTS

4,001,081  1/1977  Commeyras et al. ............... 435/129

*Primary Examiner*—Lionel M. Shapiro
*Attorney, Agent, or Firm*—Sughrue, Rothwell, Mion, Zinn and Macpeak

[57] ABSTRACT

The present invention relates to a process for producing acrylamide or methacrylamide utilizing microorganisms having a nitrilase activity. This process involves (1) utilizing highly active novel bacteria belonging to the genus Corynebacterium or the genus Nocardia, (2) conducting the reaction utilizing microorganisms having a nitrilase activity at temperatures as low as the freezing point of the medium to 15° C. so as to conduct the reaction for a long period of time while maintaining a high concentration of acrylamide or methacrylamide, and (3) conducting the reaction according to a newly devised continuous column process to obtain a highly concentrated acrylamide or methacrylamide aqueous solution with economic advantages.

18 Claims, No Drawings

PROCESS FOR PRODUCING ACRYLAMIDE OR METHACRYLAMIDE UTILIZING MICROORGANISMS

BACKGROUND OF THE INVENTION

1. Field of the Invention

The present invention relates to an improved process for producing acrylamide or methacrylamide utilizing microorganisms.

2. Description of the Prior Art

As a process for producing acrylamide or methacrylamide, there has heretofore been known a process of reacting acrylonitrile (AN) or methacrylonitrile (MAN) with water using reduced copper as a catalyst. However, it has been desired to develop a novel and industrially more advantageous process since the catalytic process involves a difficult catalyst preparation and regeneration, and the isolation and purification of the amide produced is onerous.

On the other hand, as a process for producing acrylamide or methacrylamide from acrylonitrile or methacrylonitrile utilizing an enzymatic reaction, an interesting process using bacteria belonging to the genus Bacillus, the genus Bacteridium in the sense of Prevot, the genus Micrococcus, the genus of Brevibacterium in the sense of Bergy, or the like has recently been proposed in U.S. Pat. No. 4,001,081. This process is merely based on the discovery that the above-described bacteria hydrolyze various organic nitriles to produce the corresponding organic acid amides. In the case of using acrylonitrile or methacrylonitrile (Examples 6–8 in the Patent) for example, the patent describes that acrylamide or methacrylamide was obtained almost quantitatively under the reaction conditions of: 8 to 12 wt % acrylonitrile or methacrylonitrile concentration, 2 to 4 wt % bacterial cell concentration, 7 to 9 in pH, 25° C. in temperature and 20 to 30 minutes reaction time. It is true that acrylamide or methacrylamide can be produced at a concentration as high as 10 to 20 wt %, but the bacterial cells so rapidly lose their enzymatic activity under such conditions that it is almost impossible to use them repeatedly. In addition, the solution from which the bacterial cells are separated is colored an extremely dark yellow and contains various impurities originating from the cells, and hence an onerous purifying step is necessary. Thus, the abovedescribed process is not economically advantageous in industrial applications.

SUMMARY OF THE INVENTION

A novel catalytic process for producing acrylamide or methacrylamide utilizing microorganisms has been investigated and bacteria having an extremely high activity for hydrolyzing acrylonitrile and methacrylonitrile to produce acrylamide or methacrylamide have been discovered. Namely the strain N-771 and the strain N-774 belonging to the genus Corynebacterium, and the strain N-775 belonging to the genus Nocardia have been found in the soils around the factory producing acrylonitrile and in the waste water discharged from the factory. (Hereafter the aforementioned bacteria will be referred to as N-771, N-774 and N-775, respectively.) The enzymatic nitrilase activity of these microorganisms is surprisingly high at low temperatures. As a result of intensive investigations, a process for the hydrolysis of acrylonitrile and methacrylonitrile has been developed wherein the enzymatic activity of the bacterial cells is stably maintained at a high level for a long time, with the accumulation of produced acrylamide or methacrylamide reaching concentrations as high as 10 wt % or more, which process does not require a difficult purifying step.

Thus, a principal object of the present invention is to provide a process for producing acrylamide or methacrylamide utilizing microorganisms, which comprises subjecting acrylonitrile or methacrylonitrile in an aqueous medium to microorganisms belonging to the genus Corynebacterium or the genus Nocardia and having the ability of hydrolyzing acrylonitrile or methacrylonitrile, at a temperature ranging from the freezing point of the medium to 30° C. at a pH of about 6 to 10.

Another object of the present invention is to provide a process for producing acrylamide or methacrylamide utilizing microorganisms, which comprises subjecting acrylonitrile or methacrylonitrile in an aqueous medium to microorganisms having the ability to hydrolyze acrylonitrile or methacrylonitrile to produce acrylamide or methacrylamide, at a temperature ranging from the freezing point of the medium to 15° C. at a pH of about 6 to 10.

A further object of the present invention is to provide a process for continuously producing a highly concentrated acrylamide or methacrylamide aqueous solution by passing an aqueous solution of acrylonitrile or methacrylonitrile through a column or columns filled with immobilized bacterial cells having nitrilase activity, at a temperature ranging from the freezing point of the solution to 30° C. at a pH of about 6 to 10, which comprises:

(1) using a column having one or more feed inlets provided between the column inlet and the column outlet, continuously feeding an aqueous solution of acrylonitrile or methacrylonitrile via said column inlet and, at the same time, continuously feeding acrylonitrile or methacrylonitrile via said feeding inlet(s) an amount soluble in the reaction medium; or (2) using two or a plurality of columns connected to each other in series, and continuously feeding an aqueous solution of acrylonitrile or methacrylonitrile via the first column inlet and, at the same time, continuously feeding acrylonitrile or methacrylonitrile via the column inlet(s) of the successive columns in an amount soluble in the reaction mixture.

DETAILED DESCRIPTION OF THE INVENTION

As the microorganisms used in the present invention, any one that has the ability to hydrolyze acrylonitrile or methacrylonitrile to produce acrylamide or methacrylamide may be used regardless of the taxonomic position, as well as the aforesaid strains N-771, N-774 and N-775. For example bacteria from the genus Bacillus, the genus Bacteridium, the genus Micrococcus and the genus Brevibacterium as disclosed in U.S. Pat. No. 4,001,081 may also be used. In addition, it is also possible to use the cellular extract prepared by destroying such bacterial cells, crude enzyme preparations, etc.

To culture the microorganisms used in the present invention, ordinary culture mediums containing a carbon source (e.g., glucose, maltose, etc.), a nitrogen source (e.g., ammonium sulfate, ammonium chloride, etc.), an organic nutrient source (e.g., yeast extract, malt extract, peptone, meat extract, etc.), and an inorganic nutrient source (e.g., phosphate, magnesium, potassium, zinc, iron, manganese, etc.) are used. The culture is aerobically conducted while maintaining the pH of the culture medium at about 6 to 9 at a temperature of about 20° to 35° C., preferably about 25° to 30° C., for about 1 to 5 days.

The strains N-771, N-774 and N-775 to be used in the present invention are deposited at Fermentation Research Institute, Agency of Industrial Science & Technology, Ministry of International Trade and Industry, Japan, as FERM-P Nos. 4445, 4446 and 4447, respectively. The bacteriological characteristics of each strain are as shown below.

A: STRAIN N-771

(a) Morphology (1) Shape and size of cells: $(0.5-0.8)\mu \times (2-5)\mu$
(2) Pleomorphism of cells: At the initial stage of culture, the bacterial cells are in a long bacillary form of rods without bending, and grow with snapping and, later, break and split into a coccoid or short bacillary form.
(3) Motility: none
(4) Spore: none
(5) Gram straining: positive
(6) Acid fastness: negative
(7) Metachromatic granules: positive

(b) Growth state in various culture mediums (at 30° C.)

(1) Nutrient agar plate culture: Circular (1-3 mm in diameter), with solid edges, smooth, hemispherical, opaque with luster, slightly pink.
(2) Nutrient agar slant culture: Middle growth, filament-like, surface-smooth, convex, with luster, slightly pink.
(3) Bouillon liquid culture: Vigorous growth with forming pellicle, middle-degree turbidity with growth, forming a precipitate.
(4) Bouillon gelatin stab culture: Good growth on the surface, funnel-like growth along stab, with almost no growth at the lower portion, no liquefaction of gelatin.
(5) Litmus milk: no change

(c) Physiological characteristics (1) Reduction of nitrate: positive
(2) Dentrification: negative
(3) MR test: negative
(4) VP test: negative
(5) Indole production: negative
(6) Hydrogen sulfide production: negative
(7) Hydrolysis of starch: negative
(8) Citric acid use:
Koser's culture medium: negative
Christiansen's culture medium: positive
(9) Use of inorganic nitrogen source:
Nitrate: positive
Ammonium salt: positive
(10) Pigment production: negative
(11) Urease: positive
(12) Oxidase: negative
(13) Catalase: positive
(14) Hydrolysis of cellulose: negative
(15) Growth range: pH: 5-10; temp.: 5°-37° C.
(16) Oxygen relation: aerobic
(17) O-F test: F
(18) Heat resistance (in 10% skim milk, at 72° C. for 15 minutes): none
(19) Acid and gas production from sugar

|  | Acid production | Gas production |
|---|---|---|
| L-Arabinose | + | − |
| D-Xylose | − | − |
| D-Glucose | + | − |
| D-Mannose | − | − |
| D-Fructose | + | − |
| D-Galactose | − | − |
| Maltose | − | − |
| Sucrose | − | − |
| Lactose | − | − |
| Trehalose | − | − |
| D-Sorbitol | + | − |
| D-Mannitol | + | − |
| Inositol | − | − |
| Glycerin | + | − |
| Starch | − | − |
| Salicin | − | − |

B: STRAIN N-774

(a) Morphology (1) Shape and size of cells: $(0.5-0.8)\mu \times (2-5)\mu$
(2) Pleomorphism of cells: At the initial stage of culture, the bacterial cells are in a long bacillary form of rods without bending, and grow with snapping and, later, break and split into a coccoid or short bacillary form.
(3) Motility: none
(4) Spore: none
(5) Gram straining: positive
(6) Acid fastness: negative
(7) Metachromatic granules: positive

(b) Growth state in various culture mediums (at 30° C.)

(1) Nutrient agar plate culture: Circular (1-3 mm in diameter), slightly irregular, smooth with surface-drying tendency, flat, opaque, slightly pink.
(2) Nutrient agar slant culture: Middle growth, filament-like, surface-smooth, convex with drying tendency, slightly pink.
(3) Bouillon liquid culture: Vigorous growth with forming pellicle, slight turbidity, forming a precipitate with growth.
(4) Bouillon gelatin stab culture: Good growth on the surface, funnel-like growth along stab, with almost no growth at the lower stab portion, no liquefaction of gelatin.
(5) Litmus milk: no change

(c) Physiological characteristics (1) Reduction of nitrate: positive
(2) Dentrification: negative
(3) MR test: negative
(4) VP test: negative
(5) Indole production: negative
(6) Hydrogen sulfide production: negative
(7) Hydrolysis of starch: negative
(8) Citric acid use:
Koser's culture medium: negative
Christiansen's culture medium: positive
(9) Use of inorganic nitrogen source:
Nitrate: positive
Ammonium salt: positive
(10) Pigment production: negative
(11) Urease: positive
(12) Oxidase: negative
(13) Catalase: positive
(14) Hydrolysis of cellulose: negative

(15) Growth range: pH: 5-10; temp.: 10°-40° C.
(16) Oxygen relation: aerobic
(17) O-F test: F
(18) Heat resistance (in 10% skim milk, at 72° C. for 15 minutes): none
(19) Acid and gas production from sugar

|             | Acid production | Gas production |
| ----------- | --------------- | -------------- |
| L-Arabinose | +               | −              |
| D-Xylose    | −               | −              |
| D-Glucose   | +               | −              |
| D-Mannose   | +               | −              |
| D-Fructose  | +               | −              |
| D-Galactose | −               | −              |
| Maltose     | +               | −              |
| Sucrose     | −               | −              |
| Lactose     | −               | −              |
| Trehalose   | ±               | −              |
| D-Sorbitol  | +               | −              |
| D-Mannitol  | +               | −              |
| Inositol    | −               | −              |
| Glycerin    | +               | −              |
| Starch      | −               | −              |
| Salicin     | ±               | −              |

C: STRAIN N-775

(a) Morphology (1) Shape and size of cells: (0.6-1.0)μ×(5-15)μ
(2) Pleomorphism of cells: At the initial stage of culture, the bacterial cells are in a long bacillary form with hyphalike appearance, and grow with branching and, later, break and split into a coccoid or short bacillary form.
(3) Motility: none
(4) Spore: none
(5) Gram staining: positive
(6) Acid fastness: weakly positive
(7) Metachromatic granules: positive (b) Growth state in various culture mediums (at 30° C.)

(1) Nutrient agar plate culture: Circular (1-3 mm in diameter), irregular, smooth, in relief, opaque, slightly lustrous, slightly red.
(2) Nutrient agar slant culture: Middle growth, filament-like, surface-smooth, flat trapezoid cross section with slight luster, slightly red.
(3) Bouillon liquid culture: Vigorous growth with forming pellicle, transparent solution, slightly forming a precipitate with growth.
(4) Bouillon gelatin stab culture: Good growth on the surface, funnel-like growth along stab, with almost no growth at the lower stab portion, no liquefaction of gelatin.
(5) Litmus milk: no change (c) Physiological characteristics (1) Reduction of nitrate: positive
(2) Dentrification: negative
(3) MR test: negative
(4) VP test: negative
(5) Indole production: negative
(6) Production of hydrogen sulfide: negative
(7) Hydrolysis of starch: negative
(8) Citric acid use:
Koser's culture medium: positive
Christiansen's culture medium: positive
(9) Use of inorganic nitrogen source:
Ammonium salt: positive
Nitrate: positive
(10) Pigment production: negative
(11) Urease: positive
(12) Oxidase: negative
(13) Catalase: positive
(14) Hydrolysis of cellulose: negative
(15) Growth range: pH: 6-10; temp.: 10°-40° C.
(16) Oxygen relation: aerobic
(17) O-F test: O
(18) Heat resistance (in 10% skim milk, at 72° C. for 15 minutes): none
(19) Acid and gas production from sugar:

|             | Acid production | Gas production |
| ----------- | --------------- | -------------- |
| D-Arabinose | +               | −              |
| D-Xylose    | +               | −              |
| D-Glucose   | +               | −              |
| D-Mannose   | −               | −              |
| D-Fructose  | +               | −              |
| D-Galactose | +               | −              |
| Maltose     | −               | −              |
| Sucrose     | +               | −              |
| Lactose     | −               | −              |
| Trehalose   | ±               | −              |
| D-Sorbitol  | +               | −              |
| D-Mannitol  | +               | −              |
| Inositol    | −               | −              |
| Glycerin    | +               | −              |
| Starch      | −               | −              |
| Salicin     | −               | −              |

To determine taxonomic positions of the bacteria based on the above-described bacteriological characteristics according to Bergy's Manual of Determinative Bacteriology, 7th ed. (1957) and 8th ed. (1974), the strains N-771 and N-774 fall under the aerobic, Gram-positive, non-acid fastness and catalase-positive bacillary category forming no endo-spores and no flagella. From the fact that the bacteria are in a long bacillary form at the initial stage of growth, not showing filament-like appearance but showing snapping growth without branching and that the bacteria break and split into a coccoid or short bacillary form, it is clear that they fall under the category of Coryneform bacteria. In addition, comparison with the Coryneform bacteria described in the Bergy's Manual precludes the bacteria of the present invention from belonging to: (1) the genus Cellulomonas, because they do not have cellulose-decomposing ability, (2) the genus Arthrobacter, because Gram-staining is not variable, (3) the genus Microbacterium, because they do not have heat resistance in 10% skim milk at 72° C. for 15 minutes, and (4) the genus Kurthia because they do not have flagella. Accordingly, it is concluded the bacteria of the present invention belong to the genus Corynebacterium.

The strain N-775 falls under the aerobic, Gram-positive, weakly acid fastness and catalase-positive bacillary category forming no endospores and no flagella. From the fact that the bacteria are in a long bacillary form at the initial stage of growth, showing hypha-like appearance, and grow with branching to break and split later into a coccoid or short bacillary form, they are considered to belong to the genus Nocardia.

In practicing the process of the present invention, all that is required is to select a microorganism having the ability to hydrolyze acrylonitrile or methacrylonitrile or one of the above-described microorganisms, culture it for 2 to 3 days in the aforesaid manner, collect the bacterial cells from the culture solution by centrifugation, suspend the cells in water or physiological saline and subject acrylonitrile or methacrylonitrile to the action of the cells.

That is, the reaction may usually be conducted in an aqueous suspension containing about 1 to 10 dry wt % of bacterial cells and 0.5 to 10 wt % of acrylonitrile or methacrylonitrile at a temperature ranging from about the freezing point of the medium to 30° C., preferably from about the freezing point to 15° C., at a pH of about 6 to 10, preferably about 7 to 9, for about 0.5 to 10 hours. Additionally, upon reaction, it is preferable to subsequently add acrylonitrile or methacrylonitrile as their concentration in the system falls while limiting the concentration of acrylonitrile or methacrylonitrile in the system to a level of not higher than 2 wt %, since they possess a strong toxicity and would inhibit the enzymatic reaction. Generally slightly higher concentrations of acrylonitrile and methacrylonitrile are possible with the batch process than with the continuous process described below because it is possible to stir the reaction system and a homogeneous system can be obtained.

During the reaction, the pH is preferably controlled to be in the range of about 7 to 9 by consecutively adding a caustic alkali, ammonia or the like or by previously adding a buffer solution to the system. pH values outside the above range would lead to further hydrolysis of the produced and accumulated acrylamide or methacrylamide to form by-products or would lead to reduction in stability of the cell enzyme. Thus, acrylamide or methacrylamide can be produced and accumulated with almost 100% conversion.

It is particularly noted that the accumulated concentration of produced acrylamide or methacrylamide attainable and the life of cell enzyme activity are remarkably improved by conducting the reaction at a temperature as low as the freezing point of the medium to 15° C., which is based on the following knowledge which has so far been unexpected.

That is, it has been found that: (1) the nitrilase as the hydrolase of the present invention produced and accumulated in the aforesaid bacterial cells has an extremely higher activity than generally well known hydrolases by 10 to 50 times and, therefore, the reaction can be conducted at an economical reaction rate even at temperatures as low as 15° C. or lower, (2) the enzyme of the present invention has relatively low heat resistance and it could be inactivated in an extremely short time at temperatures usually employed for ordinary enzymatic reactions (25° to 30° C.), and hence its effect is not fully exhibited when various chemical treatments are conducted to assure its stability, unless the reaction is conducted at low temperatures, (3) since the enzyme of the present invention has a relatively high activity and can react at low temperature, it is possible to remarkably reduce the enzymatic activity inhibition of acrylonitrile or methacrylonitrile and acrylamide or methacrylamide, and as a result attain concentrations of accumulatd acrylamide or methacrylamide as high as 10 to 30 wt % while stably maintaining the enzymatic activity for a long period of time.

These microorganisms may be used as intact cells but, from the standpoint of repeated use, continuous operation and purification, immobilized cells, in particular, immobilized cells entrapped by a polyacrylamide and related polymer gels, are preferred.

In conventional immobilized cells prepared by entrapping cells with polyacrylamide and related polymer, the level of enzymatic activity in the immobilized cells is 30 to 60% of the activity of intact cells in most cases. On the other hand, the cells of the present invention can be immobilized at the activity level of almost 100%, because the microorganisms are acrylamide-producing bacteria and are stable against highly concentrated acrylamide, and because immobilizing can be conducted at 15° C. or less.

The cell immobilization can be conducted by suspending the aforesaid microorganisms in a suitable aqueous medium (e.g., water, a physiological saline, a buffer solution, etc.) containing an acrylamide series monomer and a cross linking agent, adding a suitable polymerization initiator and a polymerization accelerator to the suspension, and conducting polymerization and gellation at about 0° to 30° C., preferably 0° to 15° C., at a pH of about 5 to 10, preferably about 6 to 8. The content of microorganisms in the polymerization reaction solution depends upon the kind and the form of the microorganisms used, but it is usually about 0.1 to 50 wt %, preferably about 1 to 20 dry wt %.

The acrylamide series monomers used to immobilize the cells in the present invention include, for example, acrylamide, methacrylamide, etc. and, if necessary, ethylenically unsaturated monomers copolymerizable with them may be used in combination. The concentration of such monomers in the reaction should at least be at a level high enough to form gels as a result of the polymerization, and is usually about 2 to 30 wt %, preferably about 5 to 20 wt %, based on the reaction solution.

The cross-linking agents include N,N'-methylenebisacrylamide, 1,3-di-(acrylamidomethyl)-2-imidazolidone, etc. As the polymerization initiator and the polymerization accelerator, those which least inhibit the activity of microorganisms are selected. Usually, potassium persulfate, ammonium persulfate, etc. are used as the initiator, and dimethylaminopropionitrile, triethanolamine, etc. are used as the accelerator, each in an amount of about 0.01 to 10 wt %.

Thus, there can be obtained polymer gels containing bacterial cells, i.e., immobilized cells.

The reaction of the present invention may be conducted either in a batchwise manner or in a continuous manner, but the use of the above-described immobilized cells and the continuous column process described hereinafter enables one to obtain a highly concentrated acrylamide or methacrylamide aqueous solution with extremely good industrial advantages through relatively simple procedures while stably maintaining the activity of cell enzyme for a long time.

That is, the continuous column process in accordance with the present invention comprises using one or a plurality of columns connected to each other in series, which are filled with the aforesaid immobilized cells in a density of about 0.3 to 0.5 g immobilized cells/cc. having been crushed to a suitable size (about 0.5 to 5 mm, preferably about 1 to 3 mm), continuously feeding an aqueous solution of acrylonitrile or methacrylonitrile via column inlet and, at the same time, continuously feeding acrylonitrile or methacrylonitrile at an intermediate stage or location before completion of the reaction in an amount soluble in the reaction solution. In more detail, where one column is used, a so-called sectional column having one or more feed inlets provided between the column inlet and the column outlet (one feed inlet per section), and which usually comprises a few sections, is preferable. An aqueous solution of acrylonitrile or methacrylonitrile is continuously fed via the column inlet and, at the same time, acrylonitrile or methacrylonitrile is continuously fed via all the feed inlets. A suitable feed rate is usually about 0.1 to 1.5 g AN or MAN/g cell.hr., preferably 0.3 to 0.8 g AN or MAN/g cell.hr. The amount of acrylonitrile or methacrylonitrile fed via each feed inlet is such that the acrylonitrile or methacrylonitrile added is soluble in the reaction mixture. It is preferable that the concentration of acrylonitrile or methacrylonitrile in the reaction system is limited to a level of not higher than 2 wt % since as explained above at higher concentrations it begins to have a toxic effect and inhibit the enzymatic reaction. Feeding rates in respective inlets are not necessarily the same due to the difference in the rate of consumption of acrylonitrile or methacrylonitrile during the progress of the reaction, i.e., the rates will vary depending on whether the acrylonitrile or methacrylonitrile is soluble at that particular level.

Where two or more columns are used, they are connected to each other in series, and an aqueous solution of acrylonitrile or methacrylonitrile is fed via the column inlet of the first column, and acrylonitrile or methacrylonitrile is fed via the subsequent and successive column inlet(s) in the same manner as described above. Thus, there can be obtained a highly concentrated acrylamide or methacrylamide solution as an eluate from the second or final column.

On the other hand, in the conventional continuous column process, it has been difficult to bring the bacterial cells into uniform contact with a material having a low solubility in water such as acrylonitrile of methacrylonitrile at a high concentration to react and, therefore, the conventional process suffers from the defects that a highly concentrated acrylamide or methacrylamide aqueous solution cannot be obtained effectively and smoothly, and that the enzymatic activity of the bacterial cells is sharply reduced.

Additionally, a more concentrated acrylamide or methacrylamide aqueous solution or crystals of acrylamide or methacrylamide can be obtained from the thus obtained acrylamide or methacrylamide aqueous solution of the present invention using conventional techniques. For example, the aforesaid reaction solution is treated, if necessary, with active carbon, ion-exchange resin, etc., and then concentrated under reduced pressure to obtain a more concentrated acrylamide or methacrylamide aqueous solution or crystals thereof.

The present invention will now be described in more detail by the following examples of preferred embodiments of the present invention which, however, should not be construed as limiting the present invention. Additionally, all parts and percents in the following examples are by weight. The reaction products such as acrylamide and methacrylamide, unreacted materials such as acrylonitrile and methacrylonitrile, and by-products like methacrylic acid and acrylic acid were determined by means of gas chromatography.

EXAMPLE 1

12.5 parts of the washed cells of the strain N-771 (water content: 80%) prepared by aerobic culture using a culture medium (pH: 7.2) containing 1% glucose, 0.5% peptone, 0.3% yeast extract and 0.3% malt extract, 6 parts of acrylonitrile and 81.5 parts of a 0.05 M phosphate buffer (pH: 8.8) were mixed and reacted for 1 hour at 30° C. under stirring. After the completion of the reaction, the cells were removed by centrifugation to obtain a clear solution. This solution contained 8.0% acrylamide, but contained no unreacted acrylonitrile and no by-products like acrylic acid. Thus, the reaction proceeded almost quantitatively to completion.

EXAMPLE 2

12.5 parts of the washed cells of the strain N-771 (water content: 80%) prepared in the same manner as in Example 1 were mixed with 87.5 parts of water, and acrylonitrile was continuously added dropwise thereto at a rate of 4 parts per hour while controlling the pH at 8.0 using potassium hydroxide under stirring to react at 30° C. After reacting for 2.5 hours, dropwise addition of acrylonitrile was stopped, followed by stirring for further 30 minutes. The resulting reaction solution having been reacted for further 30 minutes was centrifuged to remove the cells and obtain a clear solution. This solution contained 12.0% acrylamide, but absolutely no unreacted acrylonitrile was detected. Thus, the reaction was completed.

EXAMPLE 3

15 parts of the washed cells of the strain N-771 (water content: 80%) prepared in the same manner as in Example 1, 8 parts of methacrylonitrile and 77 parts of a 0.05 M phosphate buffer (pH: 8.8) were mixed and reacted for 1 hour at 30° C. After completion of the reaction, the cells were removed by centrifugation to obtain a clear solution. This solution contained 10.2% methacrylamide. Although a trace of methacrylic acid was detected, unreacted methacrylonitrile was not detected at all. Thus, the reaction proceeded almost quantitatively to completion.

EXAMPLE 4

12 parts of the washed cells of the strain N-774 (water content: 75%) prepared in the same manner as in Example 1 were mixed with 88 parts water, and methacrylonitrile was continuously added dropwise thereto at a rate of 3 parts per hour while controlling the pH of the solution at 8.5 using potassium hydroxide under stirring to react at 30° C. After reacting for 4 hours, dropwise addition of methacrylonitrile was discontinued, followed by stirring for further 30 minutes to almost completely react the methacrylonitrile within the system. After completion of the reaction, the cells were removed by centrifugation to obtain a clear solution. Methacrylamide in this solution was determined to be 13.0%.

EXAMPLE 5

25 parts of the washed cells (water content: 78%) of the strain N-775 prepared by aerobic culture using a culture medium (pH: 7.2) containing 1% glucose, 0.5% peptone, 0.3% yeast extract, 0.3% malt extract, 0.1% acetonitrile, 0.1% $KH_2PO_4$ and 0.05% $MgSO_4.7H_2O$, 5 parts of acrylonitrile and 70 parts of a 0.05 M phosphate buffer (pH: 8.8) were mixed and reacted for 1 hour at 30° C. under stirring. After the completion of the reaction, the cells were removed by centrifugation to obtain a clear solution. This solution contained 6.7% acrylamide, but absolutely no unreacted acrylonitrile and no by-products like acrylic acid were detected. Thus, the reaction proceeded almost quantitatively to completion.

EXAMPLE 6

8 parts of the washed cells of the strain N-771 (water content: 75%) prepared by aerobic culture using a culture medium (pH: 7.2) containing 1% glucose, 0.5% peptone, 0.3% yeast extract and 0.3% malt extract was mixed with 92 parts water, and acrylonitrile was intermittently added dropwise at a rate of 2 parts per hour while controlling the pH of the solution at 8.0 by properly adding a 0.5 N KOH aqueous solution under stirring, at various reaction temperatures ranging from about 0° C. to 30° C. as shown in Table 1. The reaction was continued until unreacted acrylonitrile was detected and, at that stage, the reaction was stopped and the cells were removed by centrifugation to obtain a clear solution. The content of acrylamide was determined with respect to each solution to compare the concentrations of accumulated acrylamide at respective reaction temperatures. Thus, the results shown in Table 1 were obtained. It is seen from the results, that the enzymatic activity of the cells became stable and the concentration of produced and accumulated acrylamide was greatly increased when the reaction was conducted at temperatures of not higher than 15° C.

Table 1

| | Run No. | | | | | |
|---|---|---|---|---|---|---|
| | 6-1 | 6-2 | 6-3 | 6-4 | 6-5 | 6-6 |
| Reaction Temperature (°C.) | −3 to 0 | 5 | 10 | 15 | 20 | 30 |
| Reaction Time Before Acrylonitrile was Detected (hrs.) | 16 | 16 | 14 | 12 | 5 | 4 |
| Acrylamide in the Reaction Solution (%) | 31.8 | 31.0 | 28.1 | 25.0 | 10.7 | 9.3 |

EXAMPLE 7

13.5 parts of the washed cells of the strain N-775 (water content: 78%) obtained by culturing in the same manner as in Example 6 were mixed with 86.5 parts water, and acrylonitrile was intermittently added dropwise at a rate of 2 parts per hour while controlling the pH of the solution at 8.0 by properly adding a 0.5 N potassium hydroxide aqueous solution under stirring, at various reaction temperatures ranging from about 0° C. to about 30° C. as shown in Table 2. Subsequently, the reaction was continued in the same manner as in Example 6 until unreacted acrylonitrile was detected. The concentration of acrylamide was determined with respect to each solution to obtain the results in Table 2. It is seen in this example, too, that the produced and accumulated acrylamide concentration greatly increased in the experiments wherein the reaction was conducted at temperature of not higher than 15° C.

Table 2

| | Run No. | | | | | |
|---|---|---|---|---|---|---|
| | 7-1 | 7-2 | 7-3 | 7-4 | 7-5 | 7-6 |
| Reaction Temperature (°C.) | −3 to 0 | 5 | 10 | 15 | 20 | 30 |
| Reaction Time Before Acrylonitrile was Detected (hrs.) | 14 | 13 | 11 | 10 | 5 | 4 |
| Acrylamide in the Reaction Solution (%) | 28.2 | 27.5 | 23.1 | 21.0 | 11.5 | 9.5 |

EXAMPLE 8

13.5 parts of the washed cells of the strain CBS 717.73 (the strain described in the Examples of U.S. Pat. No. 4,001,081) obtained by culturing in the same manner as in Example 6 (water content: 78%) was mixed with 86.5 parts water, and acrylonitrile was intermittently added dropwise at a rate of 2 parts per hour while controlling the pH of the solution at 8.0 by properly adding a 0.5 N potassium hydroxide aqueous solution under stirring, at various reaction temperatures ranging from about 0° C. to 30° C. as shown in Table 3. Subsequently, the reaction was continued in the same manner as in Example 6 until unreacted acrylonitrile was detected. The acrylamide concentration of each solution was determined. The results obtained are shown in Table 3. It is seen in this example, too, that the produced and accumulated acrylamide concentration greatly increased in the experiments wherein the reaction was conducted at temperatures of not higher than 15° C.

Table 3

| | Run No. | | | | | |
|---|---|---|---|---|---|---|
| | 8-1 | 8-2 | 8-3 | 8-4 | 8-5 | 8-6 |
| Reaction Temperature (°C.) | −3 to 0 | 5 | 10 | 15 | 20 | 30 |
| Reaction Time Before Acrylonitrile was Detected (hrs.) | 13 | 13 | 11 | 10 | 5 | 4 |
| Acrylamide in the Reaction Solution (%) | 27.5 | 26.2 | 22.9 | 21.3 | 10.2 | 9.5 |

EXAMPLE 9

4 parts of the washed cells of the strain N-771 obtained in the same manner as in Example 6, 0.45 parts of acrylamide, 0.05 part of N,N'-methylenebisacrylamide and 4 parts of physiological saline were mixed to prepare a uniform suspension. To this suspension were added 0.5 part of a 5% dimethylaminopropionitrile aqueous solution and 1 part of a 2.5% potassium persulfate aqueous solution, and the system was maintained at 10° C. for 30 minutes to polymerize. The thus obtained massive, cell-containing gels were crushed into small particles and washed with physiological saline to obtain 10 parts of immobilized cells. To 20 parts of the immobilized cells was added 72 parts of a 0.05 M phosphate buffer (pH: 8.0), and acrylontrile was dropwise added thereto at a rate of 2 parts per hour to react for 4 hours under stirring. A clear solution obtained by separating and removing the bacterial cells from the reaction product contained 10.6% acrylamide and almost no by-products like acrylic acid and unreacted acrylonitrile were detected. Thus the reaction proceeded almost quantitatively to completion.

The separated immobilized cells were repeatedly used to conduct the same reaction. On the other hand, similar experiments were conducted at 30° C. for comparison. The results obtained are shown in Table 4.

Table 4

| Number of times of repeatedly using the microorganisms | Yield of acrylamide (%) | |
|---|---|---|
| | 15° C. | 30° C. |
| 1 | 100 | 100 |
| 2 | 100 | 100 |
| 3 | 100 | 85 |
| 4 | 100 | 5 |
| 5 | 100 | 0 |
| 6 | 100 | 0 |
| 7 | 100 | 0 |

EXAMPLE 10

40 g of the immobilized cells of the strain N-771 obtained in the same manner as in Example 9 were filled in a jacketed column (3 cm in inside diameter and 25 cm in length), and a 4% acrylonitrile aqueous solution or 2.6% methacrylonitrile aqueous solution was continuously fed via the top of the column at a rate of 100 ml/hr at 10° C. and at 25° C. (for comparison) to react the times shown in Table 5. Ratios of produced acrylamide or methacrylamide at respective reaction stages were determined to obtain the results shown in Table 5.

Table 5

| Reaction Time (hr) | Yield of acrylamide (%) | | Yield of methacrylamide (%) | |
|---|---|---|---|---|
| | 10° C. | 25° C. | 10° C. | 25° C. |
| 10 | 100 | 100 | 100 | 100 |
| 20 | 100 | 32 | 100 | 100 |
| 30 | 100 | 0 | 100 | 100 |
| 40 | 100 | 0 | 100 | 4 |
| 50 | 100 | 0 | 100 | 0 |
| 100 | 100 | 0 | 100 | 0 |
| 150 | 100 | 0 | 100 | 0 |
| 200 | 100 | 0 | 100 | 0 |
| 250 | 100 | 0 | 100 | 0 |
| 300 | 100 | 0 | 100 | 0 |

EXAMPLE 11

Table 6 given below comparatively shows the activity of intact cells and of immobilized cells with respect to various microorganisms having an acrylamide-producing ability.

Preparation of immobilized cells 4 parts of intact cells (water content: 75%), 0.45 part of acrylamide, 0.05 part of N,N'-methylenebisacrylamide, and 4 parts of physiological saline were mixed to prepare a uniform suspension. To this suspension were added 0.5 part of a 5% dimethylaminopropionitrile aqueous solution and 1 part of a 2.5% potassium persulfate aqueous solution, and the system was maintained as 10° to 15° C. for 30 minutes to polymerize. Subsequently, the thus obtained cell-containing gels were crushed and washed with physiological saline to obtain 10 parts of the immobilized cells.

Measurement of the acrylamide-producing ability 0.8 part of the intact cells or 2 parts of the immobilized cells were diluted with a 0.05 M phosphate buffer (pH: 8.0) to make 100 parts. Then, 1 part of each of the thus diluted solution was mixed with 1 part of a 0.05 M phosphate buffer (pH: 8.0) containing 2% acrylonitrile and, after reacting at 10° C. for 30 minutes under stirring, acrylamide produced in the reaction solution was determined to calculate the acrylamide-producing ability of each of intact cells and immobilized cells.

Table 6

| Microorganism | Acrylamide-producing ability* | |
|---|---|---|
| | Intact cells | Immobilized cells |
| Strain N-771 genus Corynebacterium (FERM-P No. 4445) | 10.7 | 10.8 |
| Strain N-774, genus Corynebacterium (FERM-P No. 4446) | 6.0 | 5.8 |
| Strain N-775, genus Nocardia (FERM-P No. 4447) | 2.6 | 2.5 |

*Amount of acrylamide (g) produced by reacting for 1 hour per 1 g of dry bacterial cells.

EXAMPLE 12

40 parts of the washed cells of the strain N-771 (water content: 75%) prepared by aerobic culture using a culture medium (pH: 7.2) containing 1% glucose, 0.5% peptone, 0.3% yeast extract and 0.3% malt extract, 4.5 parts of acrylamide, 0.5 part of N,N'-methylenebisacrylamide and 40 parts of physiological saline were mixed to prepare a uniform suspension. To this suspension were added 5 parts of a 5% dimethylaminopropionitrile aqueous solution and 10 parts of a 2.5% potassium persulfate aqueous solution, and maintained at 10° C. for 30 minutes to polymerize. The thus obtained massive, cell-containing gels were crushed into small particles and washed well with physiological saline to obtain 100 parts of the immobilized cells.

5 jacketed columns, 3 cm inside diameter, 25 cm in length, each filled with 40 g of the immobilized cells were connected to each other in series, and a 4.5% acrylonitrile aqueous solution (using a 0.05 M phosphate buffer; pH: 8.0) was allowed to flow down via the top of column No. 1 at 10° C. at a flow-down rate of 50 ml/hr (SV$\approx$0.5 hr$^{-1}$). Subsequently, 100 parts of the eluate was mixed with 4.5 parts of acrylonitrile, and allowed to flow down via the top of column No. 2 at a flow-down rate of 52.3 ml/hr (SV$\approx$0.53 hr$^{-1}$). The eluate was then similarly allowed to consecutively flow down through column No. 3 while controlling the flow-down rate at 54.5 ml/hr (SV$\approx$0.54 hr$^{-1}$), column No. 4 at 56.8 ml/hr (SV$\approx$0.57 hr$^{-1}$), and column No. 5 at 59 ml/hr (SV$\approx$0.59 hr$^{-1}$) for 48 hours. Thus, there was continuously obtained an eluate at a reaction ratio of 100%. Additionally, the acrylamide concentration in this eluate was 25.5%.

EXAMPLE 13

7 jacketed columns, 3 cm inside diameter and 25 cm in length, filled with 40 g of the immobilized cells prepared in the same manner as in Example 12 were connected to each other in series, and a 2.5% methacrylonitrile aqueous solution dissolved in a 0.05 M phosphate buffer (pH: 8.0) was allowed to flow down through column No. 1 via the top thereof at a flow-down rate of 100 ml/hr (SV$\approx$1.00 hr$^{-1}$). Then, 100 parts of the eluate was mixed with 2.5 parts of methacrylonitrile and allowed to flow down through column No. 2 via the top thereof at a flow-down rate of 103 ml/hr (SV$\approx$1.03 hr$^{-1}$).

The eluate was then similarly allowed to consecutively flow down through column No. 3 while controlling the flow-down rate at 105 ml/hr (SV$\approx$1.05 hr$^{-1}$), column No. 4 at 108 ml/hr (SV$\approx$1.08 hr$^{-1}$), column No. 5 at 110 ml/hr (SV$\approx$1.10 hr$^{-1}$), column No. 6 at 113 ml/hr (SV$\approx$1.13 hr$^{-1}$), and column No. 7 at 115 ml/hr (SV$\approx$1.15 hr$^{-1}$) for 48 hours. The reaction ratio in this eluate was 100%, and the concentration of methacrylamide in the eluate was 19.3%.

EXAMPLE 14

45 parts of the washed cells of the strain N-775 (water content: 78%) prepared by aerobic culture using a culture medium containing 1% glucose, 0.5% peptone, 0.3% yeast extract, 0.3% malt extract, 0.1% acetonitrile, 0.1% KH$_2$PO$_4$ and 0.05% MgSO$_4$.7H$_2$O, 4.5 parts of acrylamide, 0.5 part of N,N'-methylenebisacrylamide and 40 parts of physiological saline were mixed to prepare a uniform suspension. To this were added 5 parts of a 5% dimethylaminopropionitrile aqueous solution and 10 parts of a 2.5% potassium persulfate aqueous solution, and maintained at 10° C. for 30 minutes. The thus obtained massive, cell-containing gels were crushed into small particles, and washed well with physiological saline to obtain 100 parts of the immobilized cells.

The immobilized cells were filled in a section column comprising several sections each of which had a volume of 100 ml and contained 40 g immobilized cells. A 2.5% methacrylonitrile solution (using a 0.05 M phosphate buffer; pH: 8.0) was continuously fed at a rate of 100 ml/hr via the top of the uppermost section while maintaining the temperature inside the column at 15° C., and methacrylonitrile at a rate of 3 ml/hr was added via the tops of each of sections Nos. 2 to 7 for 48 hours to conduct the reaction. In this case, no methacrylonitrile was detected in the eluate from the bottom of the 7th section of the column. Thus, the reaction was 100%. The content of methacrylamide in this eluate was 19.3%.

EXAMPLE 15

40 parts of the washed cells of the strain CBS 717.73 (the strain described in Examples of U.S. Pat. No. 4,001,081) obtained by culturing in the same manner as in Example 12 (water content: 75%), 4.5 parts of acrylamide, 0.5 part of N,N'-methylenebisacrylamide and 40 parts of physiological saline were mixed to obtain a uniform suspension. To this were added 5 parts of a 5% dimethylaminopropionitrile aqueous solution and 10 parts of a 2.5% potassium persulfate aqueous solution, and the system was maintained at 10° C. for 30 minutes to polymerize. The thus obtained massive, cell-containing gels were crushed into small particles, and well washed with physiological saline to obtain 100 parts of immobilized cells.

5 jacketed columns, 3 cm inside diameter, 25 cm in length, each filled with 40 g of the immobilized cells were connected to each other in series, and a 4.5% acrylonitrile aqueous solution (using a 0.05 M phosphate buffer; pH: 8.0) was allowed to flow down through column No. 1 via the top thereof at a temperature of 10° C. at a flow-down rate of 50 ml/hr (SV=0.5 hr$^{-1}$). Subsequently, 100 parts of the eluate was mixed with 4.5 parts of acrylonitrile, and allowed to flow down through column No. 2 via the top thereof at a flow-down rate of 52.3 ml/hr (SV$\approx$0.53 hr$^{-1}$).

The eluate was then similarly allowed to consecutively flow down through column No. 3 while controlling flow-down rate at 54.5 ml/hr (SV$\approx$0.54 hr$^{-1}$), column No. 4 at 56.8 ml/hr (SV$\approx$0.57 hr$^{-1}$), and column No. 5 at 59 ml/hr (SV$\approx$0.59 hr$^{-1}$). Analysis of the eluate from column No. 5 48 hours after the initiation of the flowing down of the solution revealed an existence of a slight amount of acrylonitrile, and the concentration of acrylamide was determined to be 24.8%.

While the invention has been described in detail and with reference to specific embodiments thereof, it will be apparent to one skilled in the art that various changes and modifications can be made therein without departing from the spirit and scope thereof.

What is claimed is:

1. A process for producing acrylamide or methacrylamide utilizing microorganisms, which comprises subjecting acrylonitrile or methacrylonitrile in an aqueous medium to the action of bacteria belonging to the genus Corynebacterium or the genus Nocardia having the ability to hydrolyze acrylonitrile or methacrylonitrile, at a temperature of from the freezing point of the medium to 30° C. at a pH of 6 to 10.

2. A process for producing acrylamide or methacrylamide utilizing microorganisms, which comprises subjecting acrylonitrile or methacrylonitrile in an aqueous medium to the action of bacteria having the ability to hydrolyze acrylonitrile or methacrylonitrile at a temperature of 15° C. or less, at a temperature of from the freezing point of the medium to 15° C. at a pH of 6 to 10.

3. The process of claim 2, wherein said microorganisms are selected from bacteria belonging to the genus Corynebacterium, the genus Nocardia, the genus Bacillus, the genus Bacteridium in the sense of Prevot, the genus Micrococcus and the genus Brevibacterium in the sense of Bergey.

4. The process of claim 3, wherein said bacteria are from the genus Corynebacterium or the genus Nocardia.

5. The process of claim 1 or 3, wherein said bacteria are of the genus Corynebacterium.

6. The process of claim 1 or 3, wherein said bacteria are of the genus Norcardia.

7. The process of claim 1 or 2, wherein said bacteria are immobilized with a polymer gel.

8. The process of claim 7, wherein said immobilized bacteria are entrapped with a polyacrylamide and related polymer gel.

9. A process for continuously producing a highly concentrated acrylamide or methacrylamide aqueous solution which comprises passing an aqueous solution of acrylonitrile or methacrylonitrile through one or more columns filled with immobilized bacterial cells having a nitrilase activity at a temperature of from the freezing point of the medium to 30° C. at a pH of 6 to 10 while feeding acrylonitrile or methacrylonitrile via one or more inlets intermediate the column inlet and outlet in an amount soluble in the reaction mixture.

10. The process of claim 9, wherein at least two columns connected in series are used and an aqueous solution of acrylonitrile or methacrylonitrile is fed to the first column inlet while acrylonitrile or methacrylonitrile are fed via the second and subsequent column inlets.

11. The process of claim 9 or 10, wherein said bacteria are selected from the group consisting of the genus Corynebacterium, the genus Nocardia, the genus Bacillus, the genus Bacteridium in the sense of Prevot, the genus Micrococcus and the genus Brevibacterium in the sense of Bergey.

12. The process of claim 9 or 10, wherein said bacteria are immobilized with a polymer gel.

13. The process of claim 12, wherein said immobilized bacteria are entrapped with a polyacrylamide and related polymer gel.

14. The process of claim 9 or 10, wherein the reaction is conducted at a temperature of from the freezing point of the medium to 15° C.

15. The process of claim 11, wherein said bacteria are from the genus Corynebacterium or the genus Nocardia.

16. The process of claim 15, wherein said bacteria are of the genus Corynebacterium.

17. The process of claim 15, wherein said bacteria are of the genus Nocardia.

18. The process of claim 1, 2, 9 or 10, wherein said bacteria are the strains N-771 or N-774 belonging to the genus Corynebacterium or the strain N-775 belonging to the genus Nocardia.

* * * * *